US00PP11574P

United States Patent [19]

Oudshoorn

[11] Patent Number: Plant 11,574

[45] Date of Patent: Oct. 17, 2000

[54] PHLOX PLANT NAMED 'LIZZY'

[75] Inventor: Herbert Oudshoorn, Rijpwetering, Netherlands

[73] Assignee: Future Plants V.O.F., Noordwijk, Netherlands

[21] Appl. No.: 09/213,446

[22] Filed: Dec. 17, 1998

[51] Int. Cl.[7] ..... A01H 5/00

[52] U.S. Cl. ..... Plt./320

[58] Field of Search ..... Plt./320

*Primary Examiner*—Howard J. Locker
*Assistant Examiner*—Michelle Kizilkaya
*Attorney, Agent, or Firm*—C. A. Whealy

[57] ABSTRACT

A distinct cultivar of Phlox plant named 'Lizzy', characterized by its upright and clumping plant habit; thick, leathery dark green leaves; distinctive red purple and white bi-colored salverform flowers; long flowering period; resistance to Powdery Mildew; and excellent garden performance.

1 Drawing Sheet

BACKGROUND OF THE INVENTION

The present invention relates to a new and distinct cultivar of Phlox plant, botanically known as *Phlox paniculata*, and hereinafter referred to by the cultivar name Lizzy.

The new Phlox was discovered by the Inventor in Rijpwetering, The Netherlands, in 1995 in a seed bed of sown *Phlox paniculata* seed from various crosses of unidentified Phlox seedling selections.

Asexual reproduction of the new cultivar by terminal cuttings taken at Rijpwetering, The Netherlands, has shown that the unique features of this new Phlox are stable and reproduced true to type in successive generations.

SUMMARY OF THE INVENTION

Plants of the cultivar Lizzy have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Lizzy'. These characteristics in combination distinguish 'Lizzy' as a new and distinct cultivar:

1. Upright and clumping plant habit.
2. Thick, leathery dark green leaves.
3. Distinctive red purple and white bi-colored salverform flowers.
4. Long flowering period, mid-summer through fall.
5. Resistance to Powdery Mildew.
6. Excellent garden performance; good weather tolerance.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a top perspective view of a typical plant of the new Phlox in outdoor cultivation. Flower and foliage colors in the photograph may appear different than the actual colors due to light reflectance.

DETAILED BOTANICAL DESCRIPTION

In the following description, color references are made to The Royal Horticultural Society Colour Chart except where general terms of ordinary dictionary significance are used. Plants used for the description were grown in 1.5-liter containers under outdoor production conditions during the spring and summer which closely approximate commercial production conditions in Rijpwetering, The Netherlands.

Botanical classification: *Phlox paniculata* cultivar Lizzy.

Parentage:

*Female parent.*—Unidentified *Phlox paniculata* seedling selection.

*Male parent.*—Unidentified *Phlox paniculata* seedling selection.

Propagation:

*Type cutting.*—Terminal vegetative cuttings.

*Time to initiate and develop roots.*—About 30 days during the spring under outdoor production conditions.

*Rooting habit.*—Numerous, fine and fleshy.

Plant description:

*Crop time.*—From cuttings, about 30 weeks are required to produce a fully-grown flowering plant in a 1.5-liter container.

*Form.*—Upright, conical, clump-forming perennial herb. Appropriate for 1.5-cm containers.

*Branching habit.*—Basally branching and also upper lateral branches.

*Plant height (from soil level to top of plant plane).*—About 55 cm.

*Area of spread.*—About 22.5 cm.

*Vigor.*—Moderate.

*Lateral branches.*—Quantity: Typically 7 to 10. Length: About 12.5 cm. Diameter: About 2 mm. Internode length: About 4 cm. Texture: Glabrous. Color: Green, 143B–143C with brownish red, 178A, overtones.

*Foliage description.*—Leaves simple, generally symmetrical, opposite and long persisting. Quantity per lateral branch: Typically about 6 to 10. Length: About 9.5 cm. Width: About 3.65 cm. Aspect: Typically horizontal. Shape: Elliptic. Apex: Acute. Base: Attenuate. Margin: Entire. Texture: Slightly ribbed, leathery and thick. Color: Young foliage, upper surface: 138A–141A. Young foliage, lower surface: 137C–137D. Mature foliage, upper surface: 137A–139A. Mature foliage, lower surface: 137C. Venation, upper surface: 137A; base of midrib, 145A. Venation, lower surface: 137C; midrib, 145A–145B. Petiole: Length: About 3.5 mm. Diameter: About 2 mm. Color: 145A.

Flower description:

*Flower type and habit.*—Single flowers arranged in terminal panicles; flowers face upright or outward. Freely flowering. Corolla, salverform, 5-lobed; calyx five-cleft. Flowers last about 5 days. Not persistent.

*Natural flowering season.*—Continuously flowering from mid-summer through fall.

*Quantity.*—Very freely flowering with 9 and 14 flowers per panicle. Usually about 75 to 90 flowers per plant.

*Fragrance.*—Faint to moderately strong; sweet.

*Flower buds.*—Length: Two days before opening, about 2.5 cm. Diameter: Two days before opening, about 7 mm. Shape: Ovate. Rate of opening: About 3 to 4 weeks from visible bud to fully opened flower. Color: 68A–68B–68C–68D to 64B.

*Flower size.*—Diameter: About 3.9 cm. Depth (tube length): About 2.25 cm.

*Corolla.*—Petal lobe length (beyond tube): About 2 cm. Petal width: About 2.25 cm. Petal quantity: Five, fused. Petal shape: Flabellate. Petal apex: Rounded. Petal margin: Entire. Petal surface: Usually flat, edges may be slightly curved upwards. Texture: Smooth; tube, sparsely pubescent. Color: Petal, upper surface, when opening: Bi-colored; red purple, 57B–58B, towards apex and white towards base forming a white "eye". Petal, lower surface, when opening: 62B–62C–62D. Petal, upper surface, opened flower: Bi-colored; red purple, 58B, towards apex; white at base forming a white "eye". Petal, lower surface, opened flower: 62B–62C–62D. Petal color, fading to: Red purple, 61C–63A, towards apex; base, light purple, 77B–77C.

*Calyx.*—Shape: Campanulate; sepals, linear, fused at base. Length: About 1.15 cm. Diameter: About 2.5 mm. Sepal quantity: Five. Sepal apex: Acuminate. Sepal margin: Entire. Texture: Smooth. Color: Upper surface: 137C. Lower surface: 143B.

*Peduncle.*—Strength: Moderate. Angle: Bent, about 10 to 30° to stem. Length: About 6.5 mm. Color: 178A.

*Reproductive organs.*—Stamens: Stamen number: Five, fused with the petals in the flower tube. Anther shape: Dorsifixed. Anther size: About 3 mm. Anther color: Creamy white. Pollen amount: Moderate. Pollen color: Creamy white. Pistils: Pistil length: About 1.8 cm. Stigma color: Light green. Style length: About 1.5 cm. Style color: Light green. Ovary color: 141A–141B.

*Seed.*—Type: Capsule. Length: About 3 mm. Diameter: About 1.5 mm. Color: Dark brown.

Weather tolerance: Plants of the new Phlox have exhibited good tolerance to rain, wind and low temperatures; good garden performance.

Disease resistance: Under commercial conditions, resistance to Powdery Mildew has been observed.

It is claimed:

1. A new and distinct cultivar of Phlox plant named 'Lizzy', as illustrated and described.

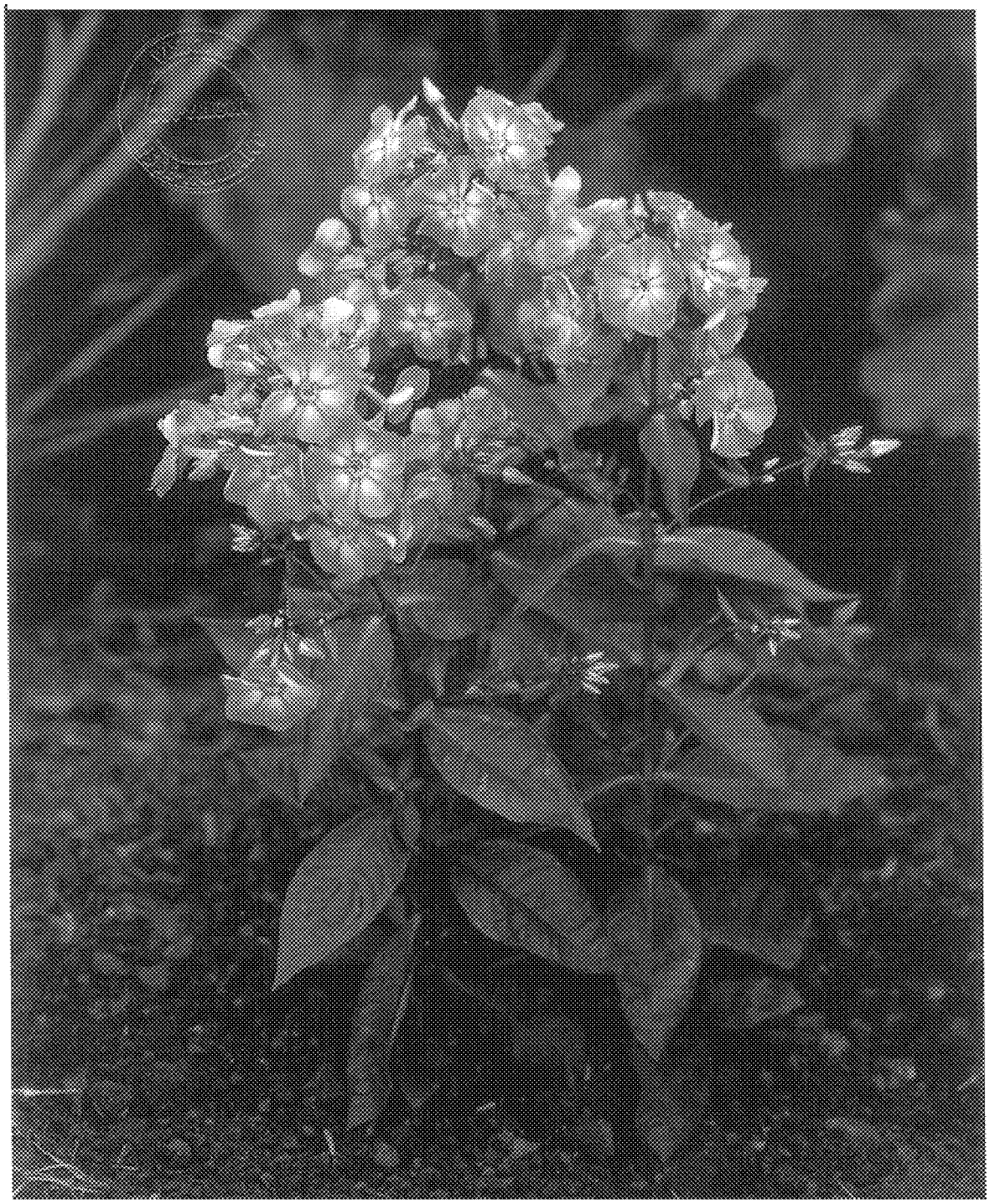

* * * * *